(12) United States Patent
Lamoncha (10) Patent No.: US 11,195,605 B2
(45) Date of Patent: Dec. 7, 2021

(54) PROVIDING GLOBAL ACCESSIBILITY TO PRESCRIBED MEDICATIONS

(71) Applicant: Mark Lamoncha, Columbiana, OH (US)

(72) Inventor: Mark Lamoncha, Columbiana, OH (US)

( * ) Notice: Subject to any disclaimer, the term of this patent is extended or adjusted under 35 U.S.C. 154(b) by 177 days.

(21) Appl. No.: 16/550,599

(22) Filed: Aug. 26, 2019

(65) Prior Publication Data

US 2021/0065864 A1   Mar. 4, 2021

(51) Int. Cl.
*G16H 20/70* (2018.01)
*G16H 70/40* (2018.01)
*G16H 20/13* (2018.01)

(52) U.S. Cl.
CPC ............ *G16H 20/13* (2018.01); *G16H 70/40* (2018.01)

(58) Field of Classification Search
CPC ........ G16H 20/13; G16H 70/40; G16H 10/60; G16H 20/17; G16H 20/30; G16H 40/20; G16H 40/60; G16H 40/63; G16H 40/67; G16H 50/20; G16H 70/20; G16H 80/00
USPC .......................................................... 705/2
See application file for complete search history.

(56) References Cited

U.S. PATENT DOCUMENTS

| | | | |
|---|---|---|---|
| 5,845,255 A | 12/1998 | Mayaud | |
| 6,523,009 B1 * | 2/2003 | Wilkins | G06Q 30/06 705/3 |
| 7,613,620 B2 | 11/2009 | Salwan | |
| 7,769,601 B1 | 8/2010 | Bleser et al. | |
| 8,335,697 B2 | 12/2012 | Siegel | |
| 8,364,504 B1 | 1/2013 | Bleser et al. | |
| 8,510,131 B1 | 8/2013 | Bleser et al. | |
| 2002/0035484 A1 | 3/2002 | Mccormick | |
| 2002/0111829 A1 | 8/2002 | Robibero | |
| 2002/0143434 A1 | 10/2002 | Greeven et al. | |
| 2003/0050802 A1 | 3/2003 | Jay et al. | |
| 2004/0006490 A1 | 1/2004 | Gingrich et al. | |
| 2004/0225527 A1 | 11/2004 | Holz | |
| 2004/0225528 A1 | 11/2004 | Brock | |
| 2005/0182656 A1 | 8/2005 | Morey | |

(Continued)

FOREIGN PATENT DOCUMENTS

WO   WO-2017139383 A1 * 8/2017 ............. G16H 10/60

OTHER PUBLICATIONS

Mara Youdelman et al., Language Services Resource Guide for Pharmacists, 2010, The National Health Law Progtam, Copyright 2010 National Health Law Program. (Year: 2010).*

(Continued)

*Primary Examiner* — Hiep V Nguyen
(74) *Attorney, Agent, or Firm* — Standley Law Group LLP (57) ABSTRACT

Systems and methods for providing world-wide access to prescribed medications are disclosed. A unique patient identifier is received and verified to match stored patient identifiers. Identification information is received and is verified to match stored information. A unique pharmacist identifier is received and is verified to match stored pharmacist identifiers. Prescriptions associated with the received unique patient identifier are displayed and one or more are selected. Dispensation information, including an amount of medication dispensed, a time and date of dispensation, and a reason for dispensation are received and the prescription database is updated accordingly.

17 Claims, 6 Drawing Sheets

(56) References Cited

U.S. PATENT DOCUMENTS

| | | | | |
|---|---|---|---|---|
| 2005/0281601 A1* | 12/2005 | Papetti | ............... | B41J 3/54 |
| | | | | 400/124.01 |
| 2008/0071572 A1 | 3/2008 | Ahmed | | |
| 2009/0106313 A1 | 4/2009 | Boldyga | | |
| 2010/0181374 A1 | 7/2010 | Martis et al. | | |
| 2013/0173280 A1* | 7/2013 | Denny | ............... | G16H 20/10 |
| | | | | 705/2 |
| 2017/0147783 A1* | 5/2017 | Carroll | ............... | G06Q 10/06 |

OTHER PUBLICATIONS

Healthlt.Gov, What is Electronic Prescribing?, https://www.healthit.gov/faq/what-electronic-prescribing, site visited Jul. 31, 2020.

American Psychiatric Association, e-Prescribing (eRX), https://www.psychiatry.org/psychiatrists/practice/practice-management/health-information-technology/e-prescribing, site visited Jul. 30, 2020.

Centers for Disease Conlrol and Prevention, Prescription Drug Monitoring Programs (PDMPs), https://www.cdc.gov/drugoverdose/pdmp/states.html, site visited Jul. 30, 2020.

\* cited by examiner

PROVIDING GLOBAL ACCESSIBILITY TO PRESCRIBED MEDICATIONS

CROSS-REFERENCE TO RELATED APPLICATIONS

This application makes no priority claim.

TECHNICAL FIELD

Exemplary embodiments relate generally to systems and methods for providing global accessibility to prescribed medications.

BACKGROUND AND SUMMARY OF THE INVENTION

Accessibility to prescribed medications is difficult to obtain when traveling. For example, one might leave for a trip and forget to pack their medication, have their prescription stolen, lose their prescription, or not realize that they only have a two-day supply left in their current prescription, but they are scheduled to be gone for a week. In such cases it may not be desirable to fully transfer a prescription to another pharmacy. Indeed, in some cases no refills are even left for a transferee pharmacy to act on. Getting in contact with the prescribing physician to have a new prescription issued is time consuming and may then require later transferring the new prescription back to the original pharmacy. This difficulty is sometimes compounded by the fact that access to the medication may be critical to ensuring appropriate care and continued health. What is needed is a system and method for providing global accessibility to prescribed medications.

A system and method for providing global accessibility to prescribed medications is disclosed herein. The prescriptions may reside on a prescription database. The prescription database may be the only database that the prescriptions may reside on during their existence, though such is not necessarily required. The prescription database may be electronically partitioned so as to provide a private, virtual storage vault for the patient's prescription(s). For example, each of the patient's prescriptions may be contained with a partitioned area of the prescription database such that the area is not shared with any other patients. In exemplary embodiments, the prescribing healthcare provider may upload a prescription directly to the patient's partitioned area within the prescription database and the prescription may be removed once dispensed or expired. In exemplary embodiments, a unique prescription identifier may be associated with each prescription uploaded to the prescription database.

A prescription database may comprise one or more of: a number of prescriptions, a list of unique patient identifiers, a list of unique pharmacist identifiers, and a list of unique healthcare providers. Identification information may be stored at the prescription database and associated with various patient identifiers. Upon receipt of a patient identifier at a pharmacy system, the prescription database may be quired to retrieve identification information associated with the received unique patient identifier. The identification information may be sent to the pharmacy system. Alternatively, or additionally, identification information may be entered at the pharmacy system and a match determination may be made against the identification information stored at the prescription database for the associated patient identifier. In exemplary embodiments, the identification information may take the form of an identification device issued to the patient following enrollment. The identification device may comprise a chip or other storage device comprising the unique patient identifier and various unique prescription identifiers associated with the patient. The identification device may be presented to the pharmacist for reading at the pharmacy system.

Prescriptions associated with the received unique patient identifier may be displayed. One or more of the displayed prescriptions may be selected. Dispensation information, including an amount of medication dispensed, a time and date of dispensation, and a reason for dispensation may be received and updated at the prescription database. The reason for dispensation may be selected from a predetermined list of reasons such as, but not limited to: lost prescription, not enough medication left, theft of medication.

Patients may be provided with read-only access to certain information stored at the prescription database associated with an entered unique patient identifier. Such information may include a list of the prescribed medications. Patients may be provided with access by way of a patient system.

Healthcare providers may be provided with write-access to certain information stored at the prescription database associated with an entered unique healthcare provider identifier. Healthcare providers may be provided with access by way of a healthcare provider system. Such write-access may be limited to the prescription information, except the dispensation information, which may be provided as read-only or not provided at all.

Pharmacists may be provided with write-access to certain information stored at the prescription database associated with an entered unique pharmacist identifier. Pharmacists may be provided with access by way of a pharmacy system. Such write-access may be limited to the dispensation information. Other information, such as a list of prescriptions associated with an entered unique patient identifier, may be provided read-only.

Each unique pharmacist identifier may be associated with a geographic area. Translation of prescription information may be provided based upon the geographic area associated with an entered unique pharmacist identifier. Furthermore, geographic specific brand names and/or generic names may be retrieved for display based upon the geographic area associated with the received pharmacist identifier.

Further features and advantages of the systems and methods disclosed herein, as well as the structure and operation of various aspects of the present disclosure, are described in detail below with reference to the accompanying figures.

BRIEF DESCRIPTION OF THE DRAWINGS

In addition to the features mentioned above, other aspects of the present invention will be readily apparent from the following descriptions of the drawings and exemplary embodiments, wherein like reference numerals across the several views refer to identical or equivalent features, and wherein.

DETAILED DESCRIPTION OF EXEMPLARY EMBODIMENT(S)

Various embodiments of the present invention will now be described in detail with reference to the accompanying drawings. In the following description, specific details such as detailed configuration and components are merely provided to assist the overall understanding of these embodiments of the present invention. Therefore, it should be apparent to those skilled in the art that various changes and modifications of the embodiments described herein can be made without departing from the scope and spirit of the present invention. In addition, descriptions of well-known functions and constructions are omitted for clarity and conciseness.

Embodiments of the invention are described herein with reference to illustrations of idealized embodiments (and intermediate structures) of the invention. As such, variations from the shapes of the illustrations as a result, for example, of manufacturing techniques and/or tolerances, are to be expected. Thus, embodiments of the invention should not be construed as limited to the particular shapes of regions illustrated herein but are to include deviations in shapes that result, for example, from manufacturing.

Figure 1:
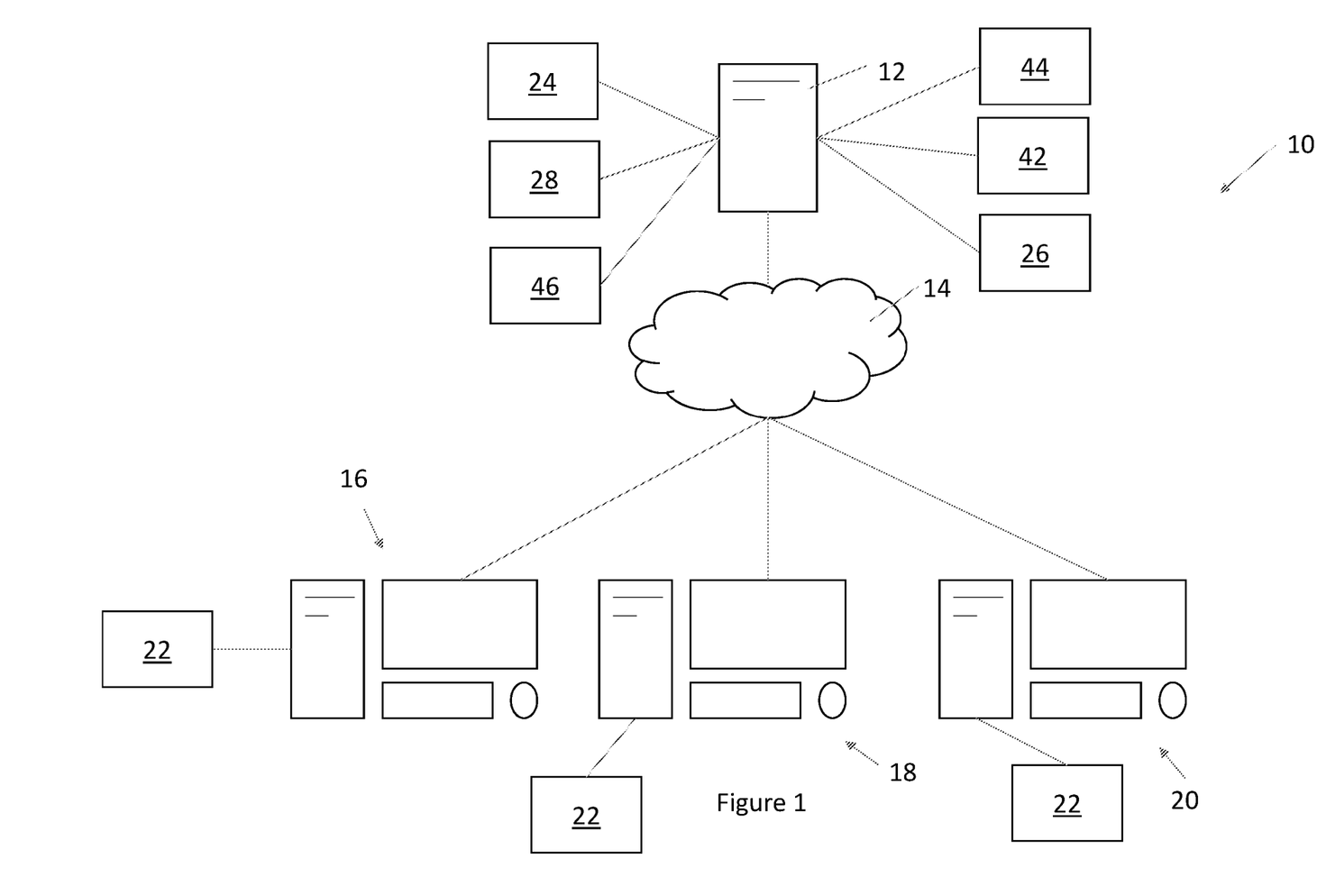
FIG. 1 is a plan view of an exemplary system.

FIG. 1 is a plan view of an exemplary system 10. The system 10 may comprise a prescription database 12. The prescription database 12 may be in electronic communication with one or more pharmacy systems 16. The prescription database 12 may be in electronic communication with one or more patient systems 18. The prescription database 12 may be in electronic communication with one or more healthcare provider systems 20. Such electronic communication may be made by way of one or more networks 14.

The prescription database 12 may comprise one or more databases, servers, processors, electronic storage devices, some combination thereof, or the like. The prescription database 12 may be cloud based storage system. The pharmacy systems 16 may each comprise one or more electronic devices such as, but not limited to, personal computers, laptops, tablet computers, smartphones, smartwatches, servers, processors, electronic storage devices, some combination thereof, or the like. The patient systems 18 may each comprise one or more electronic devices such as, but not limited to, personal computers, laptops, tablet computers, smartphones, smartwatches, servers, processors, electronic storage devices, some combination thereof, or the like. The healthcare provider systems 20 may each comprise one or more electronic devices such as, but not limited to, personal computers, laptops, tablet computers, smartphones, smartwatches, servers, processors, electronic storage devices, some combination thereof, or the like. The networks 14 may be an internet, intranet, world wide web, cellular network, some combination thereof, or the like.

Figure 2:
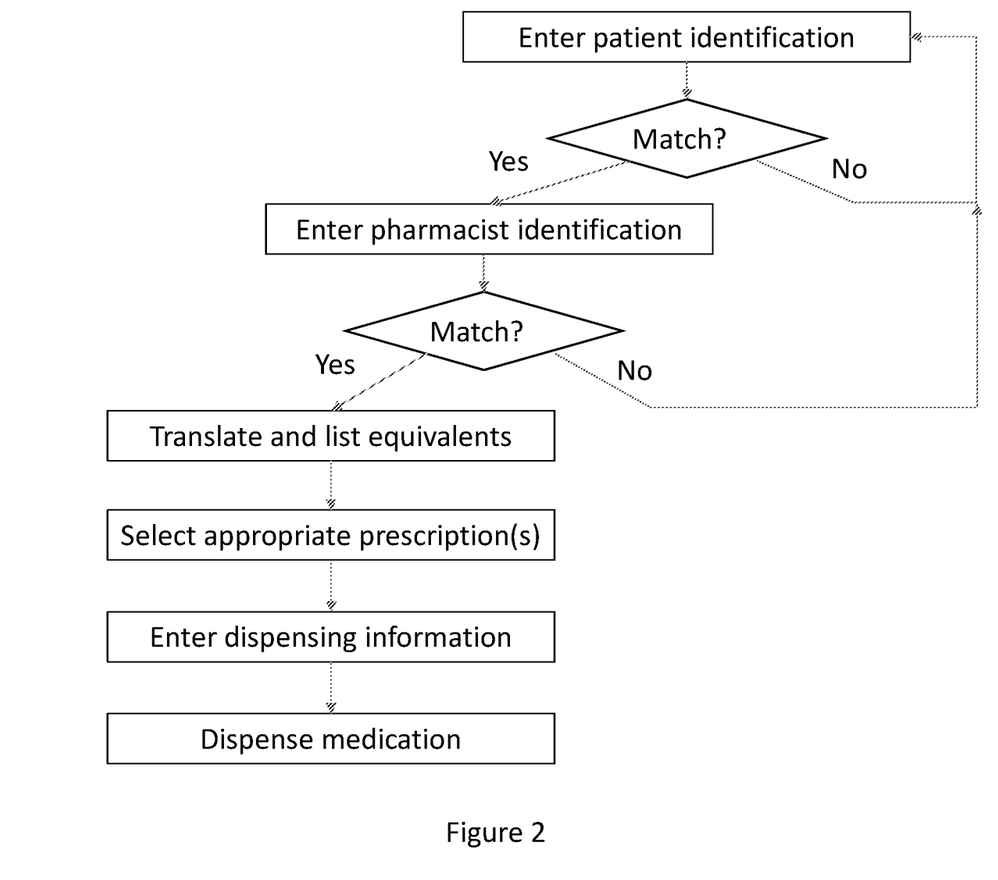
FIG. 2 is a simplified block diagram illustrating exemplary logic for dispensing a prescription using the system.

FIG. 2 is a simplified block diagram illustrating exemplary logic for dispensing a prescription using the system 10. An individual may have one or more prescriptions stored at the prescription database 12. By way of illustration, without limitation, the individual may have packed for a seven-day cruise only to realize that he or she only has two days' worth of their important heart medication left. The individual may visit the ship's pharmacy to have additional medication dispensed using the system 10. The identity of the individual may be verified.

The individual may identify himself or herself to the pharmacist or other pharmacy team member. The individual may provide a unique patient identifier for the pharmacy team member to enter into the pharmacy system 16, though such is not required.

The individual may provide one or more forms of identification to verify that they are who they say they are. Such identification may comprise, for example without limitation, a photo identification, a government issued driving license, a government issued passport, a credit card, a utility bill, some combination thereof, or the like. The pharmacy team member may enter the information at the pharmacy system 16. The information may be entered manually, or by way of one or more peripheral devices 22. The peripheral devices 22 may include, for example without limitation, magnetic strip readers, chip readers, imaging devices, some combination thereof, or the like. In exemplary embodiments, the presented forms of identification may be stored at the pharmacy database 12 in conjunction with the transaction for later review.

The entered information may be compared with stored identification information at the pharmacy database 12 to determine if identification information matching the entered information is stored at the pharmacy database 12. In exemplary embodiments, the pharmacy database 12 may compare the entered information against stored identification information associated with the provided unique patient identifier. In other exemplary embodiments, the entered identification information may be compared against all stored identification information to determine the presence or non-presence of a match.

The match determination may be performed electronically at the pharmacy database 12, though it is contemplated that such matching may instead be performed at the pharmacy system 16. For example, without limitation, a magnetic strip associated with the driver's license may be read and electronically compared for stored information at the pharmacy database 12.

If no matching information is found, such information may be displayed at the pharmacy system 16. If a match is found, such information may be displayed at the pharmacy system 16.

In other exemplary embodiments, stored identification information associated with an entered unique patient identification may be electronically transmitted from the pharmacy database 12 to the pharmacy system 16 for manual review by the pharmacy team member against the provided identification. Such stored identification information may comprise, for example without limitation, images of various forms of identification.

The identification of the dispensing pharmacy may be verified. The pharmacy team member may enter a unique pharmacist identifier at the pharmacy system 16. This unique pharmacist identifier may only be provided to pharmacy team members acting under a verified pharmacy license as further described herein. The entered unique pharmacist identifier may be evaluated against a list of unique pharmacist identifiers stored at the pharmacy database 12 to determine if a match exists. The presence or non-presence of a match may be displayed at the pharmacy system 16. In this way, both the patient's identification and the dispensing pharmacy's identification may be verified prior to access to prescription information stored at the pharmacy database 12.

Upon a successful double verification (patient and pharmacy), access to the individual's available prescriptions as listed in the pharmacy database 12 may be generated for display at the pharmacy system 16. All prescriptions available may be displayed. Prescriptions expiring may be automatically deleted from the pharmacy database 12. Furthermore, prescriptions and accounts associated with one or more individuals, medical care professionals, pharmacy team members, or other users who have not paid a service fee may be automatically deleted.

The unique pharmacist identification code may be associated with one or more languages. The prescription information may be automatically translated, by way of a human or machine translation, into the associated language. Such translation may be performed by way of a translation module 24 in electronic communication with the pharmacy database 12. In other exemplary embodiments, the translations may automatically be performed when the prescription entry is created within the system 10, and the appropriate translation may be retrieved and displayed.

The unique pharmacist identification code may be associated with one or more geographic areas. The pharmacy database 12 may be configured to associate each prescription with various equivalents, alternatives, generics, and the like for each geographic area. For example, without limitation, a prescription for a brand name drug may be written and initially dispensed from a pharmacy associated with the United States under the brand name marketed in the United States. However, Europe may have access to different equivalent or alternative drugs than the United States. Alternatively, or additionally, Europe may have the same drug marketed under a different brand or generic name. The pharmacy database 12 may be configured to automatically retrieve the brand name equivalent, alternatives, or generics available in the geographic area associated with the unique pharmacist identification code, which may or may not be available in all geographic areas. In exemplary embodiments, such language and/or geographic areas association maybe automatically determined, or verified, by the IP address of the pharmacy system 16.

Dispensing information for each prescription may be entered at the pharmacy system 16. Such dispensing information may include the identity of medications dispensed, time and date of dispensation, how many units of medication were dispensed (e.g., number of tablets, number of milliliters, etc.), some combination thereof, or the like. Such dispensing information may also comprise a reason for dispensing, which may be a mandatory entry. The reason may be selected from a predetermined list of reasons such as, but not limited to: lost prescription, not enough medication left, or theft of medication. The pharmacy database 12 may be configured to automatically flag users as potentially fraudulent who request dispensation a certain number of times within a certain time period and/or a particular reason for dispensation with a frequency above a predetermined threshold. So flagged users may be required to provide additional documentation such as, but not limited to, an affidavit, police report, statement from healthcare provider, some combination thereof, or the like. In other exemplary embodiments, some flagged users may have their related prescriptions, or all prescriptions, deleted from the prescription database 12, or may be otherwise prevented from obtaining additional medications using the system 10. In exemplary embodiment, the dispensation of each medication may be recorded by way of one or more electronic receipts stored at the prescription database 12.

In exemplary embodiments, only a portion of the prescribed medication may be dispensed. For example, just enough to get the user through their immediate needs until they can return to their regular pharmacy may be provided. If a user is traveling on a seven-day cruise and only has two days' worth of medication, for example without limitation, only five days' worth of medication may be dispensed. The pharmacy team member may be required to enter such information as part of the dispensing information. For example, without limitation, the pharmacy team member may be required to provide a detailed explanation for the number of units of medication dispensed for storage at the prescription database 12. The explanation may be associated with the dispensation. In this way, the individual's story may be subsequently verified by travel documents, credit card purchases, receipts, passport entries, some combination thereof, or the like.

This scenario is merely exemplary and is not intended to be limiting. The system and methods described herein may be utilized to fill any number and type of prescriptions such as entire prescription's, new prescriptions, refills, some combination thereof, or the like. In exemplary embodiments, certain medications, or classes of medications, such as but not limited to narcotics, may be restricted from partial fulfilment by the prescription database 12. Such restrictions may be geographic specific.

In exemplary embodiments, the prescription database 12 may be placed in electronic communication with a telemedicine module 42. The telemedicine module 42 may be configured to facilitate telemedicine visits between a patient and the healthcare provider. Such telemedicine visits may include telephonic calls, VOIP calls, video conferencing sessions, text-based exchanges, some combination thereof, or the like. In exemplary embodiments, a patient may elect to participate in a telemedicine visit by way of their patient system 18 and/or such a telemedicine visit may be required prior to filling or re-filling the prescription in question. Upon receipt of such a request, the telemedicine module 42 may be configure to automatically distribute a text message, email, scripted phone call, or other electronic notification to a number of enrolled healthcare providers, by way of the respective healthcare provider systems 20. A healthcare provider may accept the telemedicine request. After the telemedicine experience has been completed, the prescription database 12 may be configured to distribute payment to the healthcare providers. The amount disbursed may be automatically billed to the patient and/or his/her insurance provider. The telemedicine module 42 may alternatively, or additionally, be configured to facilitate in person visits, such as but not limited to, by coordinating a time, place, and healthcare provider for the visit.

The prescription database 12 may be in electronic communication with an on-call pharmacist module 44. The on-call pharmacist module 44 may be configured to automatically distribute a text message, email, scripted phone call, or other electronic notification to a number of enrolled pharmacists by way of the pharmacy systems 16. A patient may request an on-call pharmacist by way of the patient system 18. The on-call pharmacist module 44 may be configured to match patients with on-call pharmacists located nearby to dispense a prescription. A pharmacist may accept the on-call request. After the prescription is filled, the prescription database 12 may be configured to distribute payment to the pharmacist. The amount disbursed may be automatically billed to the patient and/or his/her insurance provider.

The payments and billing discussed herein may be accomplished by way of a billing module 46 in electronic communication with the prescription database 12, though such is not required. The billing module 46 may be configured to automatically generate and transmit requests for reimbursement to insurance providers, generate and transmit invoices to the patient, electronically disburse payments to providers, some combination thereof, or the like.

Figure 3:
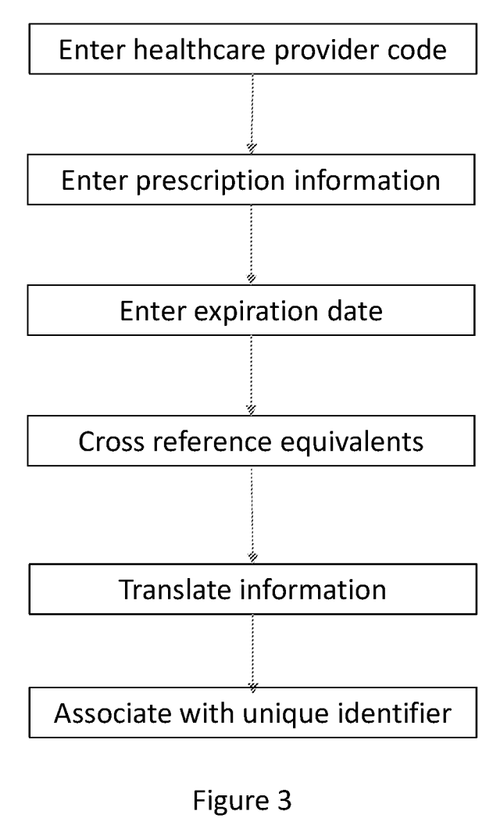
FIG. 3 is a simplified block diagram illustrating exemplary logic for entering a new prescription into the system.

FIG. 3 is a simplified block diagram illustrating exemplary logic for entering a new prescription into the system 10. A healthcare provider may initiate a new prescription within the prescription database 12 at a healthcare provider system 20. The healthcare provider may enter a unique healthcare provider identifier. The healthcare provider may enter prescription information. Such prescription information may include, for example without limitation, the name of the medication, the dosage schedule, the amount of medication to be provided, the number of refills available, some combination thereof and the like. In exemplary embodiments, the prescription information may further comprise an expiration date for each prescription. If such information is not provided, the prescription database 12 may automatically enter such expiration information. The expiration information may be automatically determined based on the classification of the drug prescribed. Table 1 provides an exemplary list, without limitation, of default expiration time tables for classes of drugs.

TABLE 1

| Class of Drug | Default Expiration |
| --- | --- |
| Narcotic | 1 month |
| Antibiotic | 6 weeks |
| Mood-altering drug | 2 months |
| Over the counter | 1 year |

Table 1 is provided as an example, without limitation. Any default expiration time for any type or class of drug is contemplated. The default expiration may be specific to the geographic region associated with the prescribing healthcare provider and/or the disbursing pharmacy. In exemplary embodiments, the prescription database 12 may be configured to automatically set the geographically relevant expiration data based on the location of the prescribing healthcare provider and/or the disbursing pharmacy.

Upon expiration, the prescription may be automatically removed from the prescription database 12. The prescription database 12 may be configured to find equivalent name brand and/or generic drugs associated with a prescribed medication for each geographic area based on information stored at the prescription database 12 or elsewhere. The prescription database 12 may be configured to automatically translate the prescription information into a number of languages by way of a human or machine translator, such as by way of the translation module 24.

In exemplary embodiments, a unique prescription identifier may be associated with each prescription uploaded to the prescription database 12. The unique identifiers described herein may be generated and assigned by a unique identifier module 28 which may be configured to create such unique identifiers. The unique identifier module 28 may be in electronic communication with the prescription database 12.

Each unique prescription identifier may be stored at the prescription database 12 in a list. Each unique prescription identifier may be associated with one or more unique patient identifiers associated with the patient for whom the prescription is written. Each unique prescription identifier may be associated with one or more unique healthcare provider identifiers associated with the prescribing healthcare provider. The unique prescription identifier may be entered, for example without limitation, by way of one or more of the pharmacy systems 16, the healthcare provider systems 20, and/or the patient systems 18 and the appropriate prescription information may be returned.

Figure 2B:
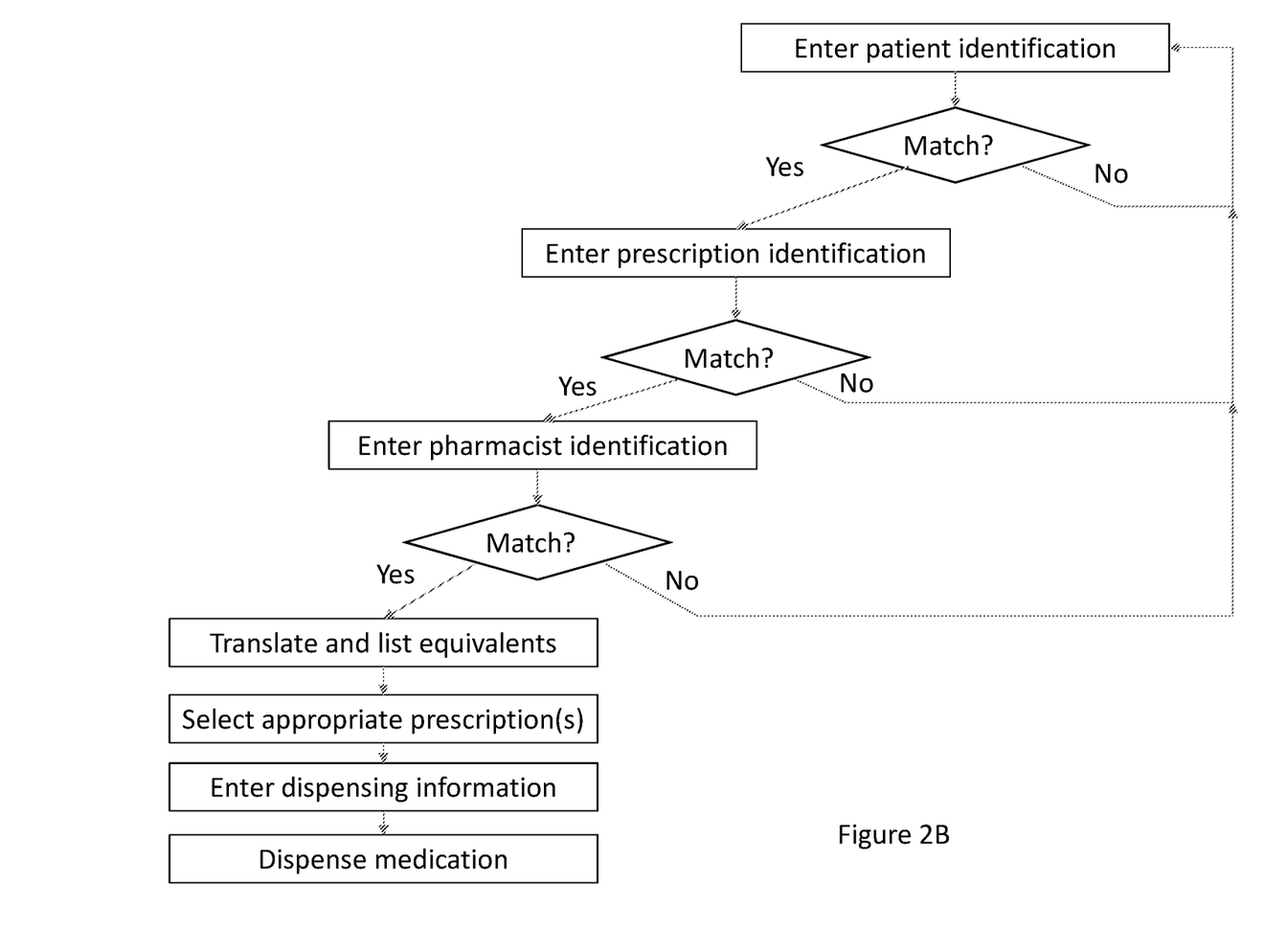
FIG. 2B is a simplified block diagram illustrating other exemplary logic for dispensing a prescription using the system.

As shown in FIG. 2B, a prompt to enter the unique prescription identifier may be generated. Upon entry, a determination may be made as to whether the entered unique prescription identifier matches one of the unique prescription identifiers stored at the prescription database 12. This may provide an additional layer of verification. First, the entered unique prescription identifier must match one stored at the prescription database 12. Second, the unique patient identifier associated with the matched unique prescription identifier as stored at the prescription database 12 may be retrieved and compared to the entered patient identifier to determine a match.

Figure 4:
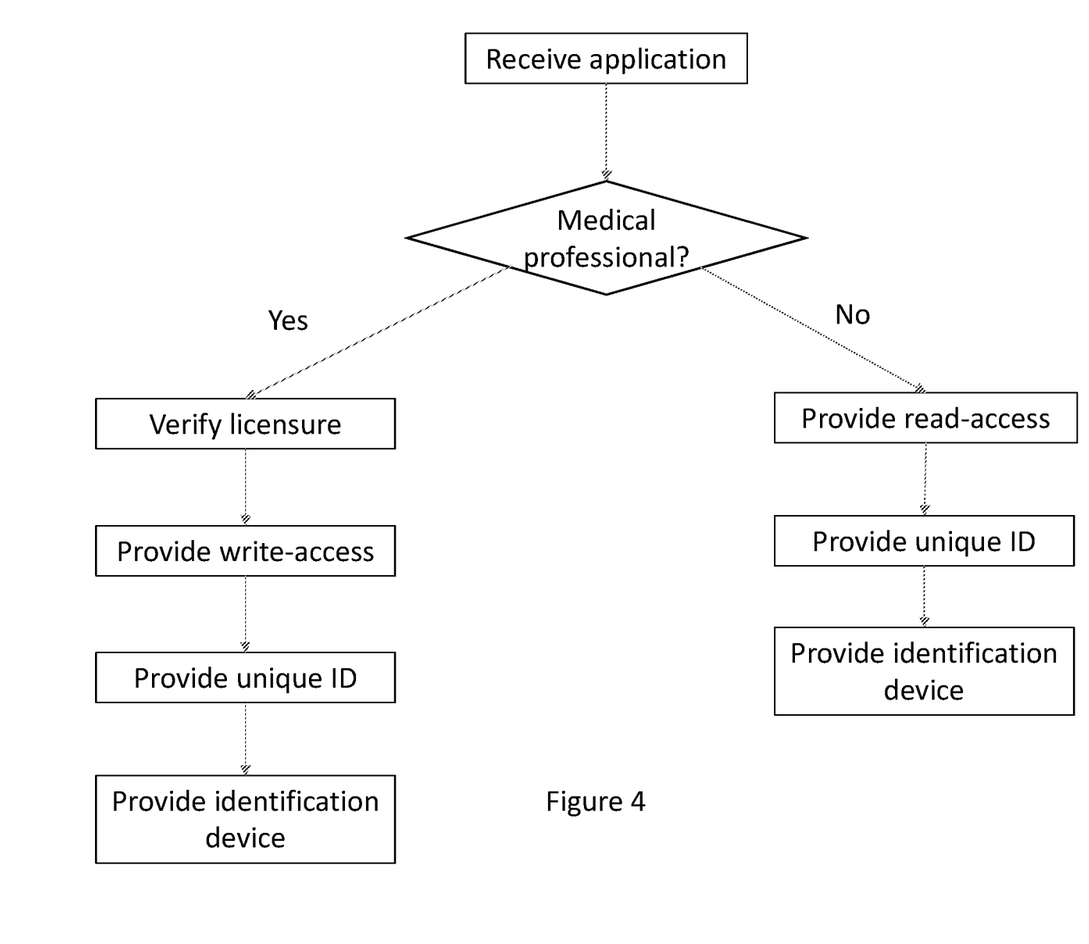
FIG. 4 is a simplified block diagram illustrating exemplary logic for adding a new user to the system.

FIG. 4 is a simplified block diagram illustrating exemplary logic for adding a new user to the system 10. An application may be received. The application may indicate whether the user is a patient, pharmacist, or healthcare provider. Each user may be tied to a unique identifier. The unique identifier may be provided only upon the provision, storage, and verification of certain identification information. A patient user may be required to provide one or more forms of identification. Such identification may comprise, for example without limitation, a photo identification, a government issued driving license, a government issued passport, a credit card, a utility bill, some combination thereof, or the like. Upon provision of such information, the patient user may be issued a unique patient identifier. Entry of the unique patient identifier, for example at the patient system 18, may grant the patient read-only access to certain information stored at the prescription database 12 and associated with the entered unique patient identifier. Such information may comprise the list of prescriptions associated with the unique patient identifier. In this way, the user may be able to retrieve and view prescriptions available.

New pharmacy users may be required to provide one or more licenses or certifications such as, but not limited to, DEA certificates or equivalent government licensure for the geographic region the pharmacy operates in. Other certifications, licensures, or the like associated with the pharmacist's licensure to dispense certain medications may be provided. The pharmacist associated with a unique pharmacist identifier may be held responsible for any and all medications dispensed under the unique pharmacist identifier.

New healthcare provider users may be may be required to provide one or more licenses or certifications such as, but not limited to, medical licenses or equivalent government licensure for the geographic region the medical professional operates in. Other certifications, licensures, or the like associated with the healthcare provider's licensure to prescribe certain medications may be provided. The healthcare provider associated with a unique healthcare provider identifier may be held responsible for any and all medications dispensed under the unique healthcare provider identifier.

The prescription database 12 may be configured to receive a unique identifier and check for the presence or non-presence of such a unique identifier at the prescription database 12. Unique identifier associated with a patient user may be granted read-only privilege as to prescriptions associated with an entered unique patient identifier. Unique identifiers associated with a pharmacy user may be granted write-privileges as related to the dispensing of medications. Unique identifier associated with a healthcare provider may be granted write-privileges as related to the generation of prescriptions. The prescription database 12 may further comprise a list of active users, who may be associated with users who have paid a service fee. When a service fee goes unpaid, the associated unique identifier may be removed from the list, or other action may be taken such that the user may no longer be able to access the prescription database 12.

Such service fees may be received by way of a payment module 26, though such is not required. The payment module 26 may be configured to receive payment information indicating the receipt of service fees. Such payment may be processed by way of credit card transactions, debit card transactions, bank transfers, electronic checks, some combination thereof, or the like.

The unique identifier may comprise a code, alphanumeric identification, a user id, a password, a digital certificate, facial recognition, finger print, or other biometric information, a one-time access code, some combination thereof, or the like. Each unique identifier may indicate one or more points of information about the underlying patient, prescription, healthcare provider, and/or pharmacist. For example, without limitation, a digit in the unique identifier may correspond with a particular geographic limitation. Another digit may correspond with a class of drug. These are merely exemplary and are not intended to be limiting.

The prescriptions may reside within the prescription database 12. The prescription database 12 may be the only database that the prescriptions reside on during their existence, though such is not required. The prescription database 12 may be electronically partitioned so as to provide a private, virtual storage vault for the patient's prescription. For example, each patient's prescription(s) may be contained with a partitioned area of the prescription database 12 such that the area is not shared with any other patients. In exemplary embodiments, the prescribing healthcare provider may upload a prescription directly to the patient's partitioned area within the database 12 and the prescription may be removed once dispensed or expired.

Figure 5:
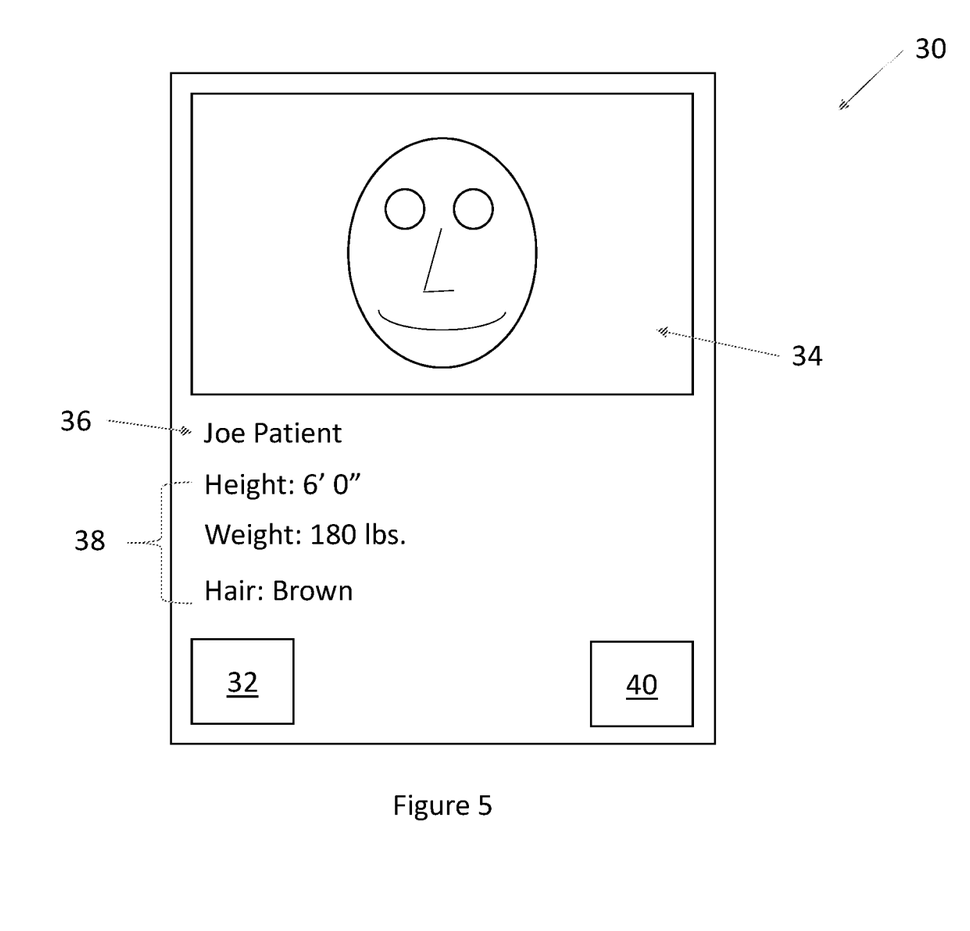
FIG. 5 is an exemplary identification device.

FIG. 5 is an exemplary identification device 30. In exemplary embodiments, the identification information described herein may take the form of an identification device 30 issued to the patient after enrollment. The identification device 30 may comprise a chip 32, magnetic strip, some combination thereof, or the like comprising the unique patient identifier and various unique prescription identifiers associated with the patient. Electronic copies of various identification documents may be stored at the chip 32 for manual comparison to presented documents. An identification device 30 may be issued to patient after successful enrolment.

The identification device 30 may be presented to the pharmacist for reading at the pharmacy system 16. Such reading may be performed at the one or more peripheral devices 22 though such is not required. Alternatively, or additionally, the identification device 30 may be presented at the patient system 18 for retrieving information associated with the unique patient identifier and/or the unique prescription identifiers. Such presentation may be made by way of an associated peripheral device 22, though such is not required. The identification device 30 may comprise additional identification information such as, but not limited to, a photo 34, identification information 36 (for example, without limitation, a name, social security number, ID number, some combination thereof, or the like), physical description information 38 (for example, without limitation, height, weight, hair color, eye color, some combination thereof, or the like), security devices 40 (for example, without limitation, watermark, hologram, some combination thereof, or the like), some combination thereof, or the like.

In exemplary embodiments, the same or similar identification device 30 may be provided to each pharmacist and/or healthcare provider following successful enrollment. The identification device 30 may comprise identification information and unique identifiers specific to the pharmacist and/or healthcare provider. The identification devices 30 may be presented to the pharmacist systems 16 and/or the healthcare provider systems 20. Such presentation may be made by way of peripheral devices 22, though such is not required.

Any embodiment of the present invention may include any of the features of the other embodiments of the present invention. The exemplary embodiments herein disclosed are not intended to be exhaustive or to unnecessarily limit the scope of the invention. The exemplary embodiments were chosen and described in order to explain the principles of the present invention so that others skilled in the art may practice the invention. Having shown and described exemplary embodiments of the present invention, those skilled in the art will realize that many variations and modifications may be made to the described invention. Many of those variations and modifications will provide the same result and fall within the spirit of the claimed invention. It is the intention, therefore, to limit the invention only as indicated by the scope of the claims.

Certain operations described herein may be performed by one or more electronic devices. Each electronic device may comprise one or more processors, electronic storage devices, executable software instructions, and the like configured to perform the operations described herein. The electronic devices may be general purpose computers or specialized computing devices. The electronic devices may be personal computers, smartphone, tablets, databases, servers, or the like. The electronic connections described herein may be accomplished by wired or wireless means.

What is claimed is:

1. A system for providing world-wide access to prescribed medications by facilitating geographic specific prescription information, said system comprising:
    a prescription database comprising:
        a list of unique patient identifiers;
        identification information associated with each of the unique patient identifiers in the list;
        one or more prescriptions associated with each of the unique patient identifiers in the list;
        a list of unique pharmacist identifiers, each of which is associated with one of multiple geographic areas, and each of the geographic areas are associated with one or more languages; and
        pharmacy certification information associated with each of the unique pharmacist identifiers in the list;
    multiple pharmacy systems in electronic communication with the prescription database;
    a translation module in electronic communication with the prescription database configured to provide machine translations between each of the one or more languages; and
    one or more non-transitory electronic storage devices associated with the prescription database and comprising software instructions, which when executed configure one or more processors to:
        receive a unique patient identifier from a particular one of the pharmacy systems;
        receive entered identification information from the particular one of the pharmacy systems;

verify that the entered identification information matches stored identification information associated with the received unique patient identifier;

receive a unique pharmacist identifier from the particular one of the pharmacy systems;

verify that the received unique pharmacist identifier matches one of the unique pharmacist identifiers stored at the prescription database;

determine the geographic area associated with the received unique pharmacist identifier;

determine the language associated with the determined geographic area;

machine translate, by way of the translation module, each of the one or more prescriptions associated with the received unique patient identifier into the determined language;

display, at the particular one of the pharmacy systems, the machine translation;

receive a user selection of one or more of the displayed prescriptions from the particular one of the pharmacy systems;

receive, from the particular one of the pharmacy systems, dispensation information comprising an amount of medication dispensed, a time and date of dispensation, and a reason for dispensation; and update, at the prescription database, the user selected prescriptions with the dispensation information.

2. The system of claim 1 wherein:

said prescription database comprises a list of medication brand names for each medication such that at least some of the medications are associated with more than one of the medication brand names, wherein each of the medication brand names for each of the medications is associated with one of the geographic areas and one or more prescriptions; and said one or more non-transitory electronic storage devices comprise additional software instructions, which when executed, configure the one or more processors to, for each retrieved prescription, retrieve a particular one of the medication brand name associated with the determined geographic area and the retrieved prescription for a particular one of the medication so that the medication brand name specific to the determined geographic area and the particular one of the medications is displayed.

3. The system of claim 2 wherein:

said list of medication brand names comprises a list of generic medication names, each associated with one of the medications and one or more geographic areas; and said one or more non-transitory electronic storage devices comprise additional software instructions, which when executed, configure the one or more processors to, for each retrieved prescription, retrieve the generic medication name associated with the determined geographic area and the particular medication.

4. The system of claim 1 wherein:

said one or more non-transitory electronic storage devices comprise additional software instructions, which when executed, configure the one or more processors to only accept dispensation information indicating an amount of medication dispensed which is less than a full prescription.

5. The system of claim 4 wherein:

said one or more non-transitory electronic storage devices comprise additional software instructions, which when executed, configure the one or more processors to, for each retrieved prescription for which fulfilment is requested:

display, at the particular one of the pharmacy systems, reasons for dispensation comprising pre-determined options for:

lost prescription;

not enough medication left; and theft of medication; and receive, from the particular one of the pharmacy systems, user selection of one of the pre-determined options, wherein the reason for dispensation comprises the user selected one of the pre-determined options.

6. The system of claim 5 wherein:

said one or more non-transitory electronic storage devices comprise additional software instructions, which when executed, configure the one or more processors to remove a unique patient identifier from the list of unique patient identifiers when one of the pre-determined options is received in association with a particular unique patient identifier with a frequency above a predetermined threshold.

7. The system of claim 1 further comprising:

a payment module in electronic communication with the prescription database and configured to receive payment information, wherein said one or more non-transitory electronic storage devices comprise additional software instructions, which when executed, configure the one or more processors to remove a unique patient identifier from the list of unique patient identifiers when payment information is not received for a particular unique patient identifier within a pre-determined amount of time.

8. The system of claim 1 wherein:

each prescription is associated with an expiration date; and said one or more non-transitory electronic storage devices comprise additional software instructions, which when executed, configure the one or more processors to:

determine a current date; and remove prescriptions associated with an expiration date prior to the current date.

9. The system of claim 8 wherein:

said one or more non-transitory electronic storage devices comprise additional software instructions, which when executed, configure the one or more processors to automatically associate a default expiration date with each prescription;

said prescription information comprises a class of drug; and said default expiration data is specific to the class of drug.

10. The system of claim 1 further comprising:

multiple patient systems, each in electronic communication with the prescription database;

multiple healthcare provider systems, each in electronic communication with the prescription database;

a list of unique healthcare provider identifiers stored at the prescription database, wherein each unique healthcare provider identifier is associated with one or more certification or licensure documents, wherein each unique healthcare provider identifier is associated with one or more unique patient identifiers, and wherein said one or more non-transitory electronic storage devices comprise additional software instructions, which when executed, configure the one or more processors to:

provide read-only access at a particular one of the patient systems which has transmitted a unique patient identifier matching one of the unique patient identifiers in the list of unique patient identifiers stored at the prescription database, wherein said read-only access is limited to information associated with the received unique patient identifier;

provide write-access with respect to the dispensation information upon receipt of a unique pharmacist identifier matching a unique pharmacist identifier stored at the prescription database, wherein said write-access is limited to dispensation information for prescriptions associated with the received unique patient identifier;

provide write-access at a particular one of the healthcare provider systems which has transmitted a unique healthcare provider identifier matching one of the unique healthcare provider identifiers in the list of unique healthcare provider identifiers stored at the prescription database, wherein said write-access is limited to prescriptions associated with unique patient identifiers associated with the transmitted unique healthcare providers.

11. The system of claim 1 wherein:
each of the unique patient identifiers comprise a user id and password; and
each of the unique pharmacist identifiers comprise a user id and password.

12. The system of claim 1 wherein:
said prescription database further comprises a list of unique prescription identifiers, wherein each of the unique prescription identifiers is associated with one of the unique patient identifiers and one of the prescriptions;
said one or more non-transitory electronic storage devices comprise additional software instructions, which when executed, configure the one or more processors to:
receive a unique prescription identifier;
determine whether the received unique prescription identifier matches one of the unique prescription identifiers stored at the list of unique prescription identifiers; and
determine whether the unique patient identifier associated with the matched unique prescription identifier matches the received unique patient identifier.

13. The system of claim 12 further comprising:
an identification device comprising one of the unique patient identifiers and one or more of the unique prescription identifiers.

14. A system for providing controlled, world-wide access to prescribed medications by facilitating geographic specific prescription information, said system comprising:
a prescription database comprising:
a list of unique patient identifiers;
identification information associated with each of the unique patient identifiers in the list;
one or more prescriptions associated with each of the unique patient identifiers in the list;
a list of unique pharmacist identifiers;
pharmacy certification information associated with each of the unique pharmacist identifiers in the list; and
multiple pharmacy systems in electronic communication with the prescription database;
one or more non-transitory electronic storage devices comprising software instructions, which when executed configure one or more processors to:
receive a unique patient identifier from a particular one of the pharmacy systems;
receive entered identification information from the particular one of the pharmacy systems;
verify that the entered identification information matches stored identification information associated with the received unique patient identifier;
receive a unique pharmacist identifier from the particular one of the number of pharmacy systems;
verify that the received unique pharmacist identifier matches one of the unique pharmacist identifiers stored at the prescription database;
display, at the pharmacy system, each of the one or more prescriptions associated with the received unique patient identifier;
receive a user selection of one or more of the displayed prescriptions from the particular one of the pharmacy systems;
display, at the particular one of the pharmacy systems, reasons for dispensation comprising pre-determined options for:
lost prescription;
not enough medication left; and
theft of medication; and
receive, from the particular one of the pharmacy systems, user selection of one of the pre-determined options;
receive, from the particular one of the pharmacy systems, dispensation information comprising an amount of medication dispensed, a time and date of dispensation, and the user selected one of the pre-determined options; and
update, at the prescription database, the user selected prescriptions with the dispensation information.

15. The system of claim 14 wherein:
said one or more non-transitory electronic storage devices comprise additional software instructions, which when executed, configure the one or more processors to remove a unique patient identifier from the list of unique patient identifiers when one of the pre-determined options is received in association with a particular unique patient identifier with a frequency above a predetermined threshold.

16. A system for providing controlled world-wide access to prescribed medications by facilitating geographic specific prescription information, said system comprising:
a prescription database comprising:
a list of unique patient identifiers;
identification information associated with each of the unique patient identifiers in the list;
one or more prescriptions associated with each of the unique patient identifiers in the list, wherein each prescription is associated with an expiration date;
a list of unique pharmacist identifiers;
pharmacy certification information associated with each of the unique pharmacist identifiers in the list; and
multiple pharmacy systems in electronic communication with the prescription database; and
one or more non-transitory electronic storage devices comprise software instructions, which when executed configure one or more processors to:
receive a unique patient identifier from a particular one of the pharmacy systems;
receive entered identification information from the particular one of the pharmacy systems;

verify that the entered identification information matches stored identification information associated with the received unique patient identifier;
receive a unique pharmacist identifier from the particular one of the number of pharmacy systems;
verify that the received unique pharmacist identifier matches one of the unique pharmacist identifiers stored at the prescription database;
display, at the pharmacy system, each of the one or more prescriptions associated with the received unique patient identifier;
receive a user selection of one or more of the displayed prescriptions from the particular one of the pharmacy systems;
receive, from the particular one of the pharmacy systems, dispensation information comprising an amount of medication dispensed, a time and date of dispensation, and a reason for dispensation;
update, at the prescription database, the user selected prescriptions with the dispensation information; and
at least once in each 24 hour period:
determine a current date; and
remove prescriptions associated with an expiration date prior to the current date.

17. The system of claim 16 wherein:

said one or more non-transitory electronic storage devices comprise additional software instructions, which when executed, configure the processor to automatically associate a default expiration date with each prescription;

said prescription information comprises a class of drug; and said default expiration data is specific to the class of drug.

* * * * *